(12) United States Patent
Liu et al.

(10) Patent No.: US 7,893,305 B2
(45) Date of Patent: Feb. 22, 2011

(54) SEPARATION OF DIOLS FROM A MIXTURE COMPRISING DIOLS AND POLYOLS

(75) Inventors: Jing Liu, Changchun (CN); Hongbin Qi, Changchun (CN); Zhouwen Xu, Changchun (CN)

(73) Assignee: Global Bio-Chem Technology Group Company Limited, Hong Kong (HK)

( * ) Notice: Subject to any disclaimer, the term of this patent is extended or adjusted under 35 U.S.C. 154(b) by 0 days.

(21) Appl. No.: 12/482,245

(22) Filed: Jun. 10, 2009

(65) Prior Publication Data

US 2010/0317902 A1    Dec. 16, 2010

(51) Int. Cl.
*C07C 29/80* (2006.01)
*C07C 27/28* (2006.01)
(52) U.S. Cl. .................. 568/868; 568/869; 568/913
(58) Field of Classification Search ............. None
See application file for complete search history.

(56) References Cited

U.S. PATENT DOCUMENTS

| | | | |
|---|---|---|---|
| 4,517,057 A | 5/1985 | Fauser et al. | |
| 5,374,716 A | 12/1994 | Biermann et al. | |
| 5,659,092 A * | 8/1997 | McNabb | 568/868 |
| 5,710,350 A | 1/1998 | Jeromin et al. | |
| 6,265,625 B1 * | 7/2001 | Vansant et al. | 568/868 |

OTHER PUBLICATIONS

Database CAPLUS on STN, Acc. No. 1962:442483, Balakhontseva et. al., Khimicheskaya Promyshlennost (St. Petersburg, Russian Federation) (1962), p. 86-88 (abstract).*
Database CAPLUS on STN, Acc. No. 2008:63282, Dziak et. al. Inzynieria i Aparatura Chemiczna (2007), 46(4-5), p. 55-59 (abstract).*

* cited by examiner

*Primary Examiner*—Brian J Davis
(74) *Attorney, Agent, or Firm*—Baker Botts LLP

(57) ABSTRACT

The present invention relates to a process for separation of diols from a mixture comprising diols and polyols, for example, from a reaction mixture obtained from hydrogenolysis of sorbitol. In particular, the present invention relates to separation of diols from the mixture using a combination of a wiped-film evaporator and a molecular evaporator to obtain diols in a high yield.

20 Claims, No Drawings

SEPARATION OF DIOLS FROM A MIXTURE COMPRISING DIOLS AND POLYOLS

FIELD OF INVENTION

The present invention relates to a process for separation of diols from a mixture comprising diols and polyols. In particular, the present invention relates to separation of diols from the mixture using a combination of a wiped-film evaporator and a molecular evaporator.

BACKGROUND OF THE INVENTION

Diols are important starting materials for a variety of industrial products such as adhesives, lubricants, polyurethanes, and coatings. Diols can be produced by various methods, including hydrogenolysis of sorbitol, glycerin and glucose. Hydrogenolysis of sorbitol can produce an assortment of alcohols, including monoalcohols of 1-4 carbons, and polyols, such as various diols of 2-4 carbons, and glycerol, as well as organic salts. As sorbitol is usually not completely converted to lower alcohols in a hydrogenolysis process, it can also be present in the resultant reaction mixture. Depending on the reaction conditions and the catalysts used in the hydrogenolysis of sorbitol, different products may be obtained, and the relative amounts of the products may also vary.

Separating diols from a mixture comprising diols and polyols (e.g., sorbitol and glycerol) can be technically challenging. Conventional distillation methods used in the industry typically require a distillation temperature of 140° C. or greater, and can achieve only around 80 to 95% yield of diols from the mixture resulting from sorbitol hydrogenolysis. The high temperature and prolonged distillation time (usually tens of minutes) can result in a substantial extent of polymerization of polyols (e.g., glycerol and sorbitol). The polymerization of these polyols, along with an increase in the concentration of the organic salts, in the distillation process can significantly raise the viscosity of the mixture, which can make the heat and mass transport in a reaction system for sorbitol hydrogenolysis more difficult. The polymerization also decreases the amount of glycerol and sorbitol reusable for the catalytic hydrogenolysis process. Glycerol can, under certain conditions of sorbitol hydrogenolysis, be converted to diols similar to those produced by hydrogenolysis of sorbitol.

Certain evaporators permit efficient separation of the components of a liquid mixture where the components of the liquid mixture are heat sensitive, e.g., susceptible to degradation or polymerization upon exposure to excessive heat. For example, a wiped-film evaporator is equipped with wiping elements for distributing a thin layer of liquid on an evaporation surface. This design greatly increases the area of the effective evaporation surface and shortens the required period of heat exposure of the liquid passing over the evaporation surface (also known as the residence time). Another type of evaporator, short-path evaporator (or molecular evaporator), has a condenser housed within its evaporator body and placed within a very short distance from an evaporation surface. Compared with a wiped-film evaporator, a molecular evaporator can typically provide higher vacuum for distillation partly because vapor leaving a liquid mixture that flows through the evaporation surface is promptly "captured" by a nearby condenser, thereby avoiding a buildup of pressure of the gas phase in a reactor.

U.S. Pat. No. 5,710,350 to Jeromin et al. ("the '350 patent") discloses a process for separating diglycerol from glycerol in polyglycerol synthesis. The process is based on condensation of diglycerol through successive steps of glycerol removal: glycerol is first separated from diglycerol, which remains in a first bottom product, in a wiped-film or short-path distillation zone at a pressure of 0.5 to 5 mbar, then the first bottom product (containing diglycerol) is further distilled in a short path distillation zone at a pressure of 0.05 to 3 mbar. The '350 patent states that about 90% or greater of diglycerol remains in the first bottom product.

Accordingly, there remains a need to develop novel and effective methods for separating diols from a mixture comprising diols and polyols to produce diols in high yields while avoiding the disadvantages of conventional distillation-based separation methods.

SUMMARY OF THE INVENTION

The present invention provides a process for separating diols from a mixture comprising diols and polyols, for example, from a reaction mixture obtained from hydrogenolysis of sorbitol. It is based, at least in part, on the discovery that diols can be separated from polyols in the mixture by a process comprising a first distillation in a wiped-film evaporator and a second distillation in a molecular (or short path) evaporator. The process includes: (a) introducing the mixture into the wiped-film evaporator; (b) distilling the mixture in the wiped-film evaporator at a pressure of about 500 to about 2000 Pa and a temperature of about 70 to about 120° C., whereby a first overhead distillate product comprising said one or more diols is obtained, and whereby a first bottom product comprising said one or more diols is formed in the wiped-film evaporator; (c) introducing the first bottom product into the molecular evaporator; and (d) distilling the first bottom product in the molecular evaporator at a pressure of about 10 to about 500 Pa and a temperature of 70 to about 130° C., whereby a second overhead distillate product comprising said one or more diols is obtained, and whereby a second bottom product is formed in the molecular evaporator.

The method can include hydrogenolysis of sorbitol to form the mixture. The method can also include removing monoalcohols and water from the mixture before introducing the mixture into the wide-film evaporator. In some embodiments, the mixture comprises 2,3-butanediol, propylene glycol, ethylene glycol, 1,2-butanediol, 1,4-butanediol, glycerol, and sorbitol.

In some embodiments, the distillation pressure in the wiped-film evaporator is about 500 to about 1000 Pa. In some embodiments, the distillation temperature in the wiped-film evaporator is about 80 to about 100° C.

In some embodiments, the distillation pressure in the molecular evaporator is about 20 to about 200 Pa. In some embodiments, the distillation temperature in the molecular evaporator is about 80 to about 125° C.

In certain embodiments, the mixture comprises one or more organic salts. The organic salts present in the mixture can be selected from the group consisting of sodium lactate, sodium formate, and sodium acetate.

The degree of polymerization of polyols (e.g., sorbitol and glycerol) can be less than 2%, preferably less than 1%, and more preferably zero. The second bottom product can comprise less than 2%, and preferably less than 1%, by weight of polymerized polyols (e.g., sorbitol and glycerol).

Diols can be produced in high yields (e.g., greater than 95%, 96%, 97%, 98% and 99%). The second bottom product can have less than 5%, and preferably less than 3%, by weight of diols.

The residence time of the mixture in the wiped-film evaporator can be about 10 to about 20 seconds. The residence time of the first bottom product in the molecular evaporator can be about 10 to about 20 seconds.

DETAILED DESCRIPTION

The present invention relates to a method for separating diols with a high yield from a liquid mixture comprising diols and polyols. A diol is an alcohol having two hydroxyl groups while a polyols is an alcohol having more than two hydroxyl groups. The method employs, in tandem, a wiped-film evaporator and a molecular evaporator. In the wiped-film evaporator, the liquid mixture is distilled and diols are obtained in the overhead distillate product. A first bottom product is also formed in the wiped-film evaporator. The first bottom product is then introduced into a molecular evaporator, where it is further distilled. Additional diols are obtained in the overhead distillate product in the molecular evaporator.

As used herein, the yield of diols refers to the total amount by weight of all separated diols, including diols in the first overhead distillate product from the wiped-film evaporator and diols in the second overhead distillate product from the molecular evaporator, relative to the total amount by weight of all diols present in the mixture. A high yield can be greater than 95%, 96%, 97%, 98% or 99%. The second bottom product can comprise less than 5%, and preferably less than 3%, by weight of diols.

The degree of polymerization of polyols refers to the total amount by weight of all polymerized polyols in the second bottom product relative to the total amount of all polyols present in the mixture. The degree of polymerization of polyols can be less than 2%, preferably less than 1%, and more preferably zero. The second bottom product can comprise less than 2%, and preferably less than 1%, by weight of polymerized polyols.

Conventional distillation-based methods generally achieve a high yield of diols at the expense of a large amount of polymerized polyols.

A wiped-film evaporator can be used for separating diols from a mixture comprising diols and polyols to reduce the residence time of the mixture such that polymerization of polyols can be reduced. However, as more diols are separated into an overhead distillate product, the remaining reaction mixture (which can contain organic salts) can become very viscous, making further separation of diols difficult. Because of the limited low pressure attainable for commercial wiped-film evaporators (around 1 KPa), to achieve a high yield of diols, an elevated temperature is necessary, which again can lead to a substantial amount of polymerized polyols that is comparable with that in conventional distillation-based methods.

A molecular evaporator is more expensive than a wiped-film evaporator because it uses higher vacuum that demands more sophisticated and expensive auxiliary vacuum instruments. Using a molecular evaporator alone to separate diols from a mixture comprising diols and polyols is economically prohibitive for industrial production. However, a combination of a wiped-film evaporator with a molecular evaporator according to the present invention provides a fast and economically effective method for separating diols from a mixture comprising diols and polyols to produce diols in a high yield with a low degree of polymerization of polyols for industrial production.

In the following, separation of diols from a reaction mixture obtained from sorbitol hydrogenolysis is used to illustrate the method according to the present invention. However, it is understood that the method can be applied to separation of diols from other mixtures comprising diols and polyols, and thus is not limited to the context of sorbitol hydrogenolysis.

Hydrogenolysis of sorbitol can be carried out by methods known in the art. Hereinafter, a mixture resulting from hydrogenolysis of sorbitol is referred to as the "reaction mixture." A reaction mixture can include water, monoalcohols, diols of 2 to 4 carbons, glycerol, sorbitol, and certain organic salts. The diols can comprise butanediols (including 1,4-butanediol, 2,3-butanediol, and 1,2-butanediol), 1,2-propanediol (or propylene glycol), and ethylene glycol. The organic salts can be sodium salts or potassium salts (e.g., sodium lactate, sodium formate, and sodium acetate). Separation of these mixed alcohols can be carried out in several stages. Monoalcohols, i.e., alcohols having only one hydroxyl group in a molecule (e.g., methanol, ethanol, and propanol), as well as water can be first removed from the reaction mixture using conventional distillation based on their relatively low boiling points. The remaining reaction mixture is hereinafter referred to as the feed reaction mixture.

In accordance with the present invention, to separate diols from a feed reaction mixture, the feed reaction mixture can be first introduced into a wiped-film evaporator, wherein it is distilled at a pressure of about 500 to about 2000 Pa, preferably at about 500 to about 1000 Pa, and more preferably at about 1000 Pa, and at a temperature of about 70 to about 120° C., preferably at about 80 to 100° C., and more preferably at about 100° C. The diols can be obtained in a first overhead distillate product in the wiped-film evaporator, and a first bottom product can be formed. The residence time of the feed reaction mixture on the evaporation surface of the wiped-film evaporator can be about 10 to about 20 seconds.

The first bottom product, which contains a reduced amount of diols as compared with the feed reaction mixture, can be further fed into a molecular evaporator and subjected to distillation at a pressure of about 10 to about 500 Pa, preferably at about 20 to about 200 Pa, and more preferably at about 200 Pa, and at a temperature of about 70 to about 130° C., preferably at about 80 to about 125° C., and more preferably at 110° C. Again, diols can be obtained in an overhead distillate product from the molecular evaporator, and a second bottom product is formed during the distillation process. The residence time of the first bottom product on the evaporation surface of the molecular evaporator can be about 10 to about 20 seconds.

The method for separating diols according to the present invention provides a high yield of diols. A high yield of diols can be greater than 95%, preferably greater than 98%, and more preferably greater than 99%. The second bottom product can comprise less than 5% by weight of diols, and preferably less than 3% by weight of diols.

The above method can also reduce polymerization of sorbitol and glycerol as compared with traditional distillation-based methods or distillation using a wiped-film evaporator alone. The degree of polymerization of sorbitol and glycerol, i.e., the percentage of the amount of polymerized sorbitol and polymerized glycerol in combination in the second bottom product out of the amount of sorbitol and glycerol in combination in the feed reaction mixture, can be less than 2%, preferably less than 1%, and more preferably, zero. The second bottom product can comprise less than 2% by weight of, and preferably less than 1% by weight of polymerized sorbitol and glycerol.

Sorbitol and glycerol can be then recycled for sorbitol hydrogenolysis, for example, they can be fed into the catalytic hydrogenolysis reaction system as starting materials.

EXAMPLES

The following Examples merely illustrate some aspects of certain embodiments of the present invention. The scope of the invention is in no way limited by the embodiments exemplified herein.

Example 1

Comparison of Different Separation Methods

Example 1 compares the experimental results obtained by three separation methods for processing a portion of the same feed reaction mixture obtained from sorbitol hydrogenolysis, i.e., the conventional distillation method, a method using a wiped-film evaporator alone, and a method according to the present invention using the combination of a wiped-film evaporator and a molecular evaporator, respectively. The differences in the yield of diols and the amount of polymerized sorbitol and glycerol obtained using these methods are summarized in Table 1.

TABLE 1

Comparisons of yields of diols and degrees of polymerization

| Separation Method | Conventional Distillation | | | Wiped-film Evaporator Alone | Combination of Wiped-film and Molecular Evaporators |
|---|---|---|---|---|---|
| Temperature (° C.) | 140 | 160 | 200 | 150 | 100 (for wiped-film evaporator) and 110 (for molecular evaporator) |
| Pressure (KPa) | 1 | 1 | 1 | 1 | 1 (for wiped-film evaporator) and 0.2 (for molecular evaporator) |
| Residence time | 15 min. | 15 min. | 15 min. | 10-20 sec. | 10-20 sec.* |
| Yield of diols (%) | 80.0 | 91.9 | 98.1 | 94 | 99.2 |
| Degree of polymerization** (%) | 9.2 | 25 | 78.1 | 15.6 | 0 |

*The residence time 10-20 sec. herein corresponds to, individually, the residence time of the feed reaction mixture in the wiped-film evaporator, and the residence time of the first bottom product in the molecular evaporator.
**The amount of polymers formed in the separation process was determined as the difference between the amount of glycerol and sorbitol in combination in the feed reaction mixture and the amount of glycerol and sorbitol in combination in the respective bottom products (in the case of separations using a wiped-film evaporator and then a molecular evaporator, the bottom product used for this determination is the second bottom product formed in the molecular evaporator). The degree of polymerization was then calculated as the amount of polymers formed divided by the total amount of glycerol and sorbitol in the feed reaction mixture. The calculations were done in the same fashion for the data presented in Tables 3 and 4 below.

The data in Table 1 show that the conventional distillation method yielded 80% diols at a distillation temperature of 140° C., accompanied by 9.2% polymerization of sorbitol and glycerol. Increasing the distillation temperature improved the yield of diols, but was attended by more severe polymerization of sorbitol and glycerol (e.g., 78.1% polymerization at a distillation temperature of 200° C.). When a wiped-film evaporator was used alone, the residence time of the feed reaction mixture was reduced to 10-20 seconds. At an elevated temperature (e.g., 150° C. as shown in the table), a yield of diols of 94% and a degree of polymerization of sorbitol and glycerol of 15.6% were obtained.

The last column of Table 1 shows the operating conditions and results obtained using the method of the present invention, wherein a wiped-film evaporator and a molecular evaporator were used in tandem. Both evaporators were operated at relatively low distillation temperature (100° C. for the wiped-film evaporator and 110° C. for the molecular evaporator), and the residence time of the processed liquid mixture was 10-20 seconds in each of the evaporators. A low pressure (or high vacuum) in the molecular evaporator (0.2 KPa) was used, and the yield of the diols reached 99.2%. Meanwhile, the polymerization of sorbitol and glycerol was not detectable.

Example 2

Component Analysis

Example 2 presents component analysis results for the products obtained by the three separation methods, i.e., the conventional distillation method, a method using a wiped-film evaporator alone, and a method according to the present invention using the combination of a wiped-film evaporator and a molecular evaporator. The operating conditions for each of these methods and the relative amounts of each component separated from the feed reaction mixture of sorbitol hydrogenolysis are summarized in Tables 2, 3, and 4.

TABLE 2

Component analysis of products obtained using a conventional distillation method

| | | Distillation Temperature (Temp. at the Bottom Column)(° C.) | | | | | |
|---|---|---|---|---|---|---|---|
| | | 140 | | 160 | | 200 | |
| | | Pressure (Pa) | | | | | |
| | | 1000 | | 1000 | | 1000 | |
| | | Compound (wt. %) | | | | | |
| | Feed | Overhead Product | Bottom Product | Overhead Product | Bottom Product | Overhead Product | Bottom Product |
| 2,3-Butanediol | 2.5 | 3.5 | 1.2 | 3.5 | 0.6 | 3.5 | 0.2 |
| Propylene glycol | 43.3 | 60.2 | 20.4 | 60.3 | 10.2 | 60.2 | 2.9 |
| Ethylene glycol | 22.2 | 30.9 | 10.4 | 30.9 | 5.2 | 30.9 | 1.5 |
| 1,2-Butanediol | 3.9 | 5.4 | 1.8 | 5.4 | 0.9 | 5.4 | 0.3 |
| 1,4-Butanediol | 0.3 | | 0.7 | | 0.9 | | 1.0 |
| Glycerol | 3.9 | | 8.7 | | 9.2 | | 4.0 |
| Sorbitol | 11.2 | | 23.7 | | 24.4 | | 7.6 |
| Lactate | 3.7 | | 8.7 | | 10.9 | | 12.5 |
| Formate | 6.7 | | 15.8 | | 19.8 | | 22.7 |
| Acetate | 2.2 | | 5.2 | | 6.5 | | 7.5 |
| Polymer | | | 3.3 | | 11.2 | | 40.0 |
| Overall weight percent of the overhead or bottom product (%) | | 58.0 | 42.0 | 66.1 | 33.9 | 70.5 | 29.5 |

TABLE 2-continued

Component analysis of products obtained using a conventional distillation method

| | Distillation Temperature (Temp. at the Bottom Column)(° C.) | | | | | |
|---|---|---|---|---|---|---|
| | 140 | | 160 | | 200 | |
| | Pressure (Pa) | | | | | |
| | 1000 | | 1000 | | 1000 | |
| | Compound (wt. %) | | | | | |
| | Feed | Overhead Product | Bottom Product | Overhead Product | Bottom Product | Overhead Product | Bottom Product |
| Yield of diols (%) | | 80.7 | | 91.9 | | 98.1 | |
| Degree of polymerization (%) | | | 9.2 | | 25 | | 78.1 |

TABLE 3

Component analysis of products obtained using a wiped-film evaporator

| Distillation Temperature (Temp. at the Bottom Column) (° C.) | 150 | | |
|---|---|---|---|
| Pressure (Pa) | 1000 | | |
| Compound (wt. %) | Feed | Overhead Product | Bottom Product |
| 2,3-Butanediol | 2.5 | 3.5 | 0.5 |
| Propylene glycol | 43.3 | 60.2 | 8.0 |
| Ethylene glycol | 22.2 | 30.9 | 4.1 |
| 1,2-Butanediol | 3.9 | 5.4 | 0.7 |
| 1,4-Butanediol | 0.3 | | 0.9 |
| Glycerol | 3.9 | | 10.2 |
| Sorbitol | 11.2 | | 28.3 |
| Lactate | 3.7 | | 11.4 |
| Formate | 6.7 | | 20.7 |
| Acetate | 2.2 | | 6.8 |
| Polymer | | | 8.3 |
| Overall weight percent of the overhead or bottom product (%) | | 67.6 | 32.4 |
| Yield of diols (%) | | 94 | |
| Degree of polymerization (%) | | | 15.6 |

TABLE 4

Component analysis of products obtained using a wiped-film evaporator and then a molecular evaporator

| | Wiped-film evaporator | Molecular evaporator | Wiped-film evaporator | Molecular evaporator | Wiped-film evaporator | Molecular evaporator |
|---|---|---|---|---|---|---|
| | Distillation Temperature (Temp. at the Bottom Column)(° C.) | | | | | |
| | 100 | 130 | 100 | 110 | 100 | 90 |
| | Pressure (Pa) | | | | | |
| | 1000 | 200 | 1000 | 100 | 1000 | 20 |
| | Compound (wt. %) | | | | | |

| | Feed | Overhead Product | Bottom Product | Overhead Product | Bottom Product | Overhead Product | Bottom Product |
|---|---|---|---|---|---|---|---|
| 2,3-Butanediol | 2.5 | 3.5 | 0.1 | 3.5 | 0.1 | 3.5 | 0.1 |
| Propylene glycol | 43.3 | 60.2 | 1.4 | 60.0 | 1.5 | 60.0 | 1.4 |
| Ethylene glycol | 22.2 | 30.9 | 0.7 | 30.8 | 0.8 | 30.8 | 0.7 |
| 1,2-Butanediol | 3.9 | 5.4 | 0.1 | 5.4 | 0.1 | 5.4 | 0.1 |
| 1,4-Butanediol | 0.3 | | 0.7 | 0.1 | 0.7 | 0.1 | 0.7 |
| Glycerol | 3.9 | | 13.4 | 0.3 | 13.1 | 0.1 | 13.4 |
| Sorbitol | 11.2 | | 38.4 | | 39.3 | | 39.4 |
| Lactate | 3.7 | | 13.0 | | 13.0 | | 13.0 |
| Formate | 6.7 | | 23.6 | | 23.5 | | 23.6 |
| Acetate | 2.2 | | 7.7 | | 7.7 | | 7.7 |
| Polymer | | | 0.5 | | 0.0 | | 0.0 |

TABLE 4-continued

Component analysis of products obtained using a wiped-film evaporator and then a molecular evaporator

| | | Wiped-film evaporator | Molecular evaporator | Wiped-film evaporator | Molecular evaporator | Wiped-film evaporator | Molecular evaporator |
|---|---|---|---|---|---|---|---|
| | | \multicolumn{6}{c}{Distillation Temperature (Temp. at the Bottom Column)(° C.)} |
| | | 100 | 130 | 100 | 110 | 100 | 90 |
| | | \multicolumn{6}{c}{Pressure (Pa)} |
| | | 1000 | 200 | 1000 | 100 | 1000 | 20 |
| | | \multicolumn{6}{c}{Compound (wt. %)} |
| | Feed | Overhead Product | Bottom Product | Overhead Product | Bottom Product | Overhead Product | Bottom Product |
| Overall weight percent of the overhead or bottom product (%) | | 71.2 | 28.8 | 71.6 | 28.4 | 71.5 | 28.5 |
| Yield of diols (%) | | 99 | | 99.2 | | 99.1 | |
| Degree of polymerization (%) | | | 1.3 | | 0 | | 0 |

In Table 4, the "overhead product" refers to the combination of the overhead distillate products obtained from the wiped-film evaporator and the molecular evaporator, and the "bottom product" refers to the second bottom product formed in the molecular evaporator.

As used in the present application, the term "about" means within an acceptable error range for the particular value as determined by one of ordinary skill in the art, which will depend in part on how the value is measured or determined, i.e., the limitations of the measurement system. It can mean a variation of up to 10%, preferably up to 5%, and more preferably up to 1% of a given reference value.

The foregoing merely illustrates the principles of the presently claimed invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the present invention and are thus within the spirit and scope of the present invention. All publications cited herein are hereby incorporated by reference in their entireties.

What is claimed is:

1. A process for separating one or more diols from a feed mixture comprising one or more diols and one or more polyols, comprising:
    a) introducing the feed mixture into a wiped-film evaporator;
    b) distilling the feed mixture in the wiped-film evaporator at a pressure of about 500 to about 2000 Pa and a temperature of about 70 to about 120° C., whereby a first overhead distillate product comprising a first portion of said one or more diols is obtained, and whereby a first bottom product comprising a second portion of said one or more diols is formed in the wiped-film evaporator;
    c) introducing the first bottom product into a molecular evaporator; and
    d) distilling the first bottom product in the molecular evaporator at a pressure of about 10 to about 500 Pa and a temperature of about 70 to about 130° C., whereby a second overhead distillate product comprising at least some of the second portion of said one or more diols is obtained, and whereby a second bottom product is formed in the molecular evaporator.

2. The process of claim 1, wherein the distillation pressure in the wiped-film evaporator is about 500 to about 1000 Pa.

3. The process of claim 1, wherein the distillation temperature in the wiped-film evaporator is about 80 to about 100° C.

4. The process of claim 1, wherein the distillation pressure in the molecular evaporator is about 20 to about 200 Pa.

5. The process of claim 1, wherein the distillation temperature in the molecular evaporator is about 80 to about 125° C.

6. The process of claim 1, wherein the feed mixture further comprises one or more organic salts.

7. The process of claim 6, wherein the organic salts are selected from the group consisting of sodium lactate, sodium formate, and sodium acetate.

8. The process of claim 1, whereby the second bottom product comprises less than 2% by weight of polymerized said one or more polyols.

9. The process of claim 1, whereby the second bottom product comprises less than 5% by weight of said one or more diols.

10. The process of claim 1, whereby the yield of all diols separated by the process is greater than 95%, relative to the total amount by weight of all diols in the feed mixture.

11. The process of claim 10, whereby the yield of all diols separated by the process is greater than 99%, relative to the total amount by weight of all diols in the feed mixture.

12. The process of claim 1, wherein the residence time of the feed mixture in the wiped-film evaporator is about 10 to about 20 seconds.

13. The process of claim 1, wherein the residence time of the first bottom product in the molecular evaporator is about 10 to about 20 seconds.

14. The process of claim 1, further comprising hydrolysis of sorbitol to form the feed mixture.

15. The process of claim 14, further comprising removing monoalcohols and water from the feed mixture prior to introducing the feed mixture into the wiped-film evaporator.

16. The process of claim 14, wherein the feed mixture comprises 2,3-butanediol, propylene glycol, ethylene glycol, 1,2-butanediol, 1,4-butanediol, glycerol, and sorbitol.

17. The process of claim 14, whereby the second bottom product comprises less than 2% by weight of polymerized sorbitol and glycerol.

18. The process of claim 14, whereby the second bottom product comprises less than 5% by weight of said one or more diols.

19. The process of claim 14, whereby the yield of all diols separated by the process is greater than 95%, relative to the total amount by weight of all diols in the feed mixture.

20. The process of claim 19, whereby the yield of all diols separated by the process is greater than 99%, relative to the total amount by weight of all diols in the feed mixture.

* * * * *